(12) United States Patent
Bird et al.

(10) Patent No.: US 6,307,147 B1
(45) Date of Patent: Oct. 23, 2001

(54) ORGANIC DYES FOR PHOTOVOLTAIC CELLS AND FOR PHOTOCONDUCTIVE ELECTROPHOTOGRAPHY SYSTEMS

(75) Inventors: George R. Bird, Princeton; Ronald Raymond Sauers, Highland Park; Paul Panayotatos, New Brunswick, all of NJ (US)

(73) Assignee: Rutgers, The State University of New Jersey, Piscataway, NJ (US)

( * ) Notice: Subject to any disclaimer, the term of this patent is extended or adjusted under 35 U.S.C. 154(b) by 0 days.

(21) Appl. No.: 09/551,764

(22) Filed: Apr. 18, 2000

Related U.S. Application Data

(63) Continuation of application No. 08/984,135, filed on Dec. 3, 1997, now Pat. No. 6,051,702, which is a continuation-in-part of application No. 08/852,929, filed on May 8, 1997, now abandoned.

(51) Int. Cl.[7] ..................... H01L 31/036; H01L 31/0256; H01L 31/04
(52) U.S. Cl. ........................... 136/263; 136/256; 257/40; 257/431
(58) Field of Search ..................................... 136/263, 256; 257/40, 431; 540/122, 123, 124, 125; 544/350

(56) References Cited

U.S. PATENT DOCUMENTS 4,061,654 * 12/1977 Idelson ................................ 540/122

(List continued on next page.)

FOREIGN PATENT DOCUMENTS

| 267711 | 1/1969 | (AT) . |
| WO 99/03868 | * 1/1999 | (WO) . |

OTHER PUBLICATIONS

C.K. Hsiao, et al., "Performance Characteristics of Hydroxygallium Phthalocyanine–based Xerographic Photoreceptors", (1994) IS&T's Tenth International Congress on Advances in Non–Impact Printing Technologies, pp. 220–222.

(List continued on next page.)

Primary Examiner—Alan Diamond
(74) Attorney, Agent, or Firm—Davidson, Davidson & Kappel, LLC

(57) ABSTRACT

Photovoltaic cells disclosed comprising a structure according to formula I as shown below:

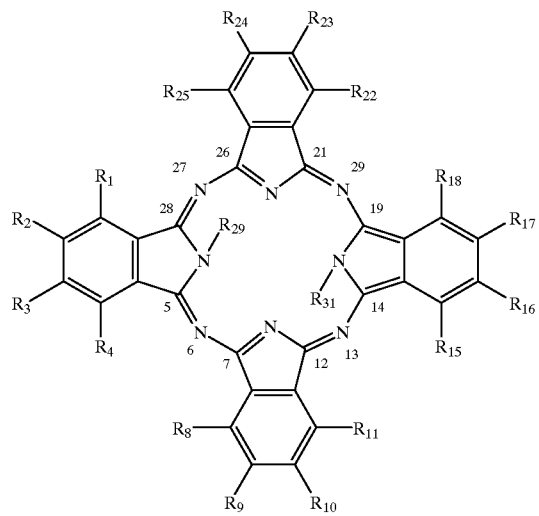

wherein $R_1$, $R_4$, $R_8$, $R_{11}$, $R_{15}$, $R_{18}$, $R_{22}$, and $R_{25}$ are selected from the group consisting of hydrogen, fluorine, chlorine, methoxy, methyl, ethyl and cyano; wherein $R_{31}$ and $R_{29}$ are both hydrogen or together are a metal ion having a double positive charge or a metal ion plus non-metal atom or group bound to the metal ion, and having overall a double positive charge; and wherein $R_1$, $R_4$, $R_{15}$, and $R_{18}$ are the same and are a first substituent, and $R_8$, $R_{11}$, $R_{22}$ and $R_{25}$ are the same and are a second substituent which is different from said first substituent.

19 Claims, 6 Drawing Sheets

U.S. PATENT DOCUMENTS

| | | |
|---|---|---|
| 4,458,004 | 7/1984 | Tanikawa . |
| 4,701,396 | 10/1987 | Hung et al. . |
| 4,898,799 | 2/1990 | Fujimaki et al. . |
| 5,153,313 | 10/1992 | Kazmaier et al. . |
| 5,164,493 | 11/1992 | Mayo et al. . |
| 5,393,629 | 2/1995 | Nukada et al. . |
| 5,407,766 | 4/1995 | Mayo et al. . |
| 5,473,064 | 12/1995 | Mayo et al. . |
| 6,043,428 * | 3/2000 | Han et al. ............................ 136/263 |
| 6,051,702 * | 4/2000 | Bird et al. ............................ 540/122 |

OTHER PUBLICATIONS

A.M. Richter, et al., "New Perylenetetracarboxylic Acid Bisimides as Charge Generation Pigments for Electrophotography", (1994) IS&T's Tenth International Congress on Advances in Non–Impact Printing Technologies, pp. 246–248.

J.B. Whitlock, et al., "Investigations of materials and device structures for organic semiconductor solar cells", vol. 32, No. 8, Aug. 1993, Optical Engineering, pp. 1921–1934.

J.D. Mayo, et al., "Preparative Study of Hydroxygallium Phthalocyanine", (1994) IS&T's Tenth International Congress on Advances in Non–Impact Printing Technologies, pp. 223–226.

N. Kobayashi, et al., "Phthalocyanines of a Novel Structure . . . ", 1994, American Chemical Society, pp. 1735–1740.

T.I. Martin, et al., Solvent Induced Transformation of the Polymorphs of Oxytitanium Phthalocyanine (TiOPo), Proceedings of IS&T's Eleventh International Congress on Advances in Non–Impact Printing Technologies, vol. 11, pp 30–35 (date unknown).

J.G. Young, et al., "Synthesis and Characterization of Di–d–isubstituted Phthalocyanines", 1990, American Chemical Society, pp. 2155–2159.

P.M. Kazmaier, et al., "A Theoretical Study of Crystallochromy. Quantum Interference Effects in the Spectra of Perylene Pigments", (1994) American Chemical Society, vol. 116, pp. 9684–9691.

J.B. Whitlock, et al., "Hydration of chloroaluminum phthalocyanine", Thin Solid Films, vol. 215, (1992) pp. 84–87.

I. Leznoff, et al., "Phthalocyanines" (1989), VCH Publishers, Inc., pp. 6–53.

P.Kazmaier, "The Interaction of Synthesis and Molecular Simulation. The Development of Design Rules for Photoreceptor Materials Synthesis", IS&T NIP12: Int'l Conf. on Digital Printing Technologies, (1997).

K. Daimon, et al., "A New Polymorph of Hydroxy Gallium Phthalocyanine and its Application for Photoreceptor", (1994), IS&T's Tenth International Congress on Advances in Non–Impact Printing Technologies, pp. 215–219.

G. Bird, "A Critical Test of Organic P–N Photovoltaic Cells," Conference Booklet, National Renewable Energy Laboratory of the U.S. Department of Energy, Estes Park, Colorado (Feb. 5–8, 1996).

* cited by examiner

ORGANIC DYES FOR PHOTOVOLTAIC CELLS AND FOR PHOTOCONDUCTIVE ELECTROPHOTOGRAPHY SYSTEMS

This application is a continuation of U.S. Ser. No. 08/984,135, filed Dec. 3, 1997, issued as U.S. Pat. No. 6,051,702 which is a continuation in part of U.S. Ser. No. 08/852,929, filed May 8, 1997, now abandoned.

BACKGROUND OF THE INVENTION

This invention relates to improved phthalocyanine compounds (Pc's) used as dyes for applications as solar organic photovoltaic (OPV) materials and as electrophotographic (Xerographic) organic photoconductor (OPC) materials.

Phthalocyanines, or Pc's, are compounds used as dyes in various applications. Metal-free Pcs have the general formula set forth below:

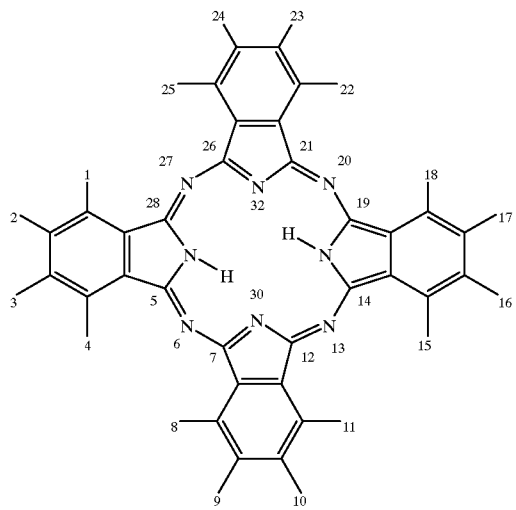

The integers represent the numbering scheme for the positions of the ring substituents and other positions and is taken from C. C. Leznoff and A. B. P. Lever in *Phthalocyanines, Properties and Applications* (1989). The "inner" positions for the Pc ring substituents are those closest to the core, and are identified as positions 1, 4, 8, 11, 15, 18, 22 and 25. The "outer" positions are 2, 3, 9, 10, 16, 17, 23 and 24.

Unsubstituted metal-free Pc's, where the inner and outer positions are all occupied by H atoms, are planar. The four benzene rings lie symmetrically about the line of the four-fold symmetry axis, which is projected vertically outward from the centroid of the N atoms of the Pc molecule.

Favorable examples of photoconducting Pc's that have been used in the prior art include metal-free $H6_2Pc$ and especially $X-H_2.Pc$ which is an unstable but long-lived crystal structure(polymorph) produced by shearing the stable (β) or another unstable (α) crystal structure.

Metallophthalocyanines have the general formula set forth below:

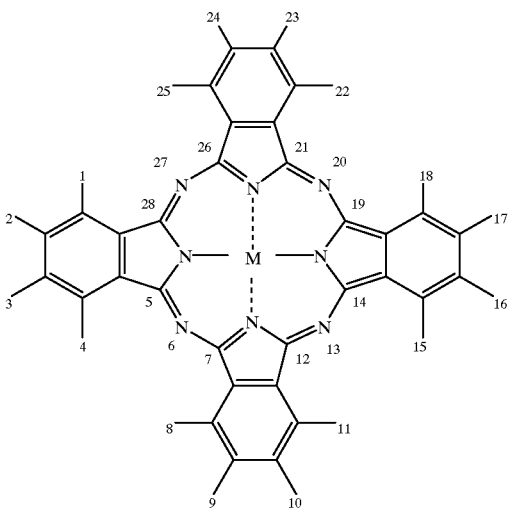

wherein M represents a metal ion or metal ion plus non-metal atom or group bound to the metal ion, and may be for example 2 Li+; Mg++; Ni++; Cu++; Zn++; Al++—Cl; V++=O; Ga++—Cl; Ga++—OH; $Ti^{++}$=O; and In++—Cl. Like unsubstituted metal-free Pc, an unsubstituted metallized Pc containing a divalent metal ion in its core is normally a planar molecule. However, where M is a metal ion and a non-metal atom or group bound to the metal ion, the non-metallic atom bound to the metal atom (=O, —OH, —Cl) projects from the plane of the metallophthalocyanine and is sometimes referred to as the "pin" of the molecule. CuPc is a particularly common metallophthalocyanine, so durable that it can be used to dye asphalt roofing shingles blue. The metallophthalocyanines use the same integer numbering system as metal-free phthalocyanines, but their numbering stops at position 28.

One of the problems associated with the use of ring-substituted Pc's is the inherent inefficiency of many Pc compounds. For example, "heavy atoms", with large nuclear charges, cause what is known as intersystem crossing, i. e., the change of spin with the transition of energy of excitons via dissipative processes into low energy spin systems, such as triplet states, and thus are undesirable as either substituent groups or as "pins." Thus Br, with an atomic number of 35, and I, with an atomic number of 53 are disfavored as pins, and In metal, with an atomic number of 49, and Tl metal, with an atomic number of 81, are disfavored for this reason for use as core atoms. Generally elements with a valence of +3 or +4, beginning with Al, with an atomic number of 13 and ending shortly above Ga, with an atomic number of 31, are favored.

Further, it has been determined that it is generally unfavorable for the unexcited state of the M group to be paramagnetic. Thus, in some respects copper, in the form Cu++, and vanadium, in the form V++=O, are disfavored though both have had the benefit of extensive trials for electrophotography.

It is also desired that the core compound result in a stable end material. One problem with prior art metallophthalocyanines is that some of them form hydrates with the addition of water molecule(s) from the atmosphere, and can then later lose the water molecule and revert to their prior state of hydration as a function of the relative humidity of water in the atmosphere. Thus, as explained in J. Whitlock, et al., *Thin Solid Films* Vol. 215, pp. 84–87 (1992), ClAlPc is disfavored because it is inherently unstable at mid-range humidities, and has a tendency to form a more efficient dihydrate which can later recycle with reduced water content in dry air.

Metallized Pc's that are known in the prior art, as described in Inami, et al., 39 *J. Imaging Sci. and Tech.* 39 (1995), include ClAlPc, ClGaPc, ClInPc, HOGa-Pc, TiOPc, and HOGaPc. All of these compounds, with the possible exception of HOGaPC, also appear to take up water to form hydrates.

One significant problem with prior art methods of the synthesis of ring-substituted Pc's has been the inability to control the symmetry of the Pc compound, or similarly the inability to limit the synthesis product to a formation of a single isomeric product. Since each isomer is likely to have three or more polymorphs, the formation of a mixture of isomers is to be avoided if at all possible. Here we identify rigid Pc molecules such as CuPc and $H_2Pc$ which can form three or more quite different crystal structures having quite different absorption spectra and X-ray diffraction patterns. When any one of these polymorphs is dissolved or vaporized and then re-solidified, various mixtures of the polymorphs may be deposited.

Multiple isomers are all too easily formed with the use of a phthalonitrile having a single substituent, such as either of 3-chlorophthalonitrile or 4-chlorophthalonitrile, to form a Pc compound. For example, the prior art reaction of Cu with the unsubstituted o-phthalonitrile (1,2-dicyanobenzene), results in a metallophthalocyanine structure as depicted above where M is Cu. The initial step of the reaction forms around a positive core, which may be a protonated amine of the formula $R_2NH_2^+$, which is then replaced by two hydrogen ions $2H^+$ to give an overall planar, metal free Pc formula of $C_{32}H_{18}N_8$. Thereafter, a divalent metal ion or group such as $Cu^{++}$ may be added to replace the two central hydrogens, resulting in an overall formula suggesting the four-fold symmetry around the positive core $(=Cu^{++})$ of $C_{32}H_{16}N_8Cu$. However, when the introduction of four identical substituents through reaction with a single monosubstituted phthalonitrile is attempted, as with 3-chlorophthalonitrile, the synthesis produces up to four isomeric tetrachlorophthalocyanines with the addition of a single component. Consequently, the resulting mixture of isomers may include one or more potentially useful molecules, but their useful properties may be lost in the mixture of isomers. One such isomer might be 1,11,18,25-tetrachlorophthalocyanine. Melting or vaporizing a solid phthalocyanine may not change the concentrations of isomers, and a variety of polymorphs may form at any solidification, depending on various factors including the isomer composition, the rate of cooling and the kinds of surfaces available for condensation. The system does not crystallize reproducibly. Prior art methods of Pc synthesis have not utilized a solution to the problem of obtaining a single, desired polymorph of a Pc ring compound. For example, C. C. Leznoff and A. B .P. Lever, in "Phthalocyanines, Properties and Applications," (1989) (hereinafter referred to as Levenoff, et al.), which is hereby incorporated by reference, did not use symmetrical substitutions on either the outer or inner benzo-ring positions and thus made isomeric mixtures even in their most favored cases. It is noted that the example of synthesis by their Scheme VII is acknowledged to give a mixture of 2,16 and 2,17 diphenyl di-substituted Pc's. Leznoff, et al. describes high overall reaction yields when relatively small groups are added as substituents on the inner positions of the Pc ring.

U.S. Pat. No. 4,061,654, to Idelson, describes two symmetrical substituted intermediate materials, a 3,6-diethylphthalonitrile and a 3,6-dimethylphthalonitrile in column 9, line 50 and column 10, line 25. However, the Idelson reference has no sample synthesis which uses only pairs of inner substituents of suitably small groups. Further, Idelson is directed to making mixtures of chemical isomers which is advantageous for controllable textile dyes, but disadvantageous for organic photoconductors or photovoltaic materials.

K. Watanabe, et al., in "Syntheses and Properties of Titanyl Phthalocyanine, New Polymorphs," Ninth Conference on Non-Impact Printing, Society for Imaging Science and Technology, pp. 659–62, (1993), discusses the production of a "Y-polymorph" of titanylphthalocyanine. It is believed that the actual compound is the monohydrate $TiOPc.H_2O$. Watanabe also discusses the preparation of 4F—, 4Cl—or $4NO_2$—derivatives. However, the methods described in Watanabe do not fix the location of the four fluorine atoms, except to the extent that one F atom is substituted on each benzene ring. Thus, the supposed single compound of pure $F_4TiOPc$ can actually be a mixture of four isomers with partially randomized substituent locations. When a monosubstituted phthalonitrile such as 3-chlorophthalonitrile or 4-chlorophthalonitrile is used, multiple isomers will be encountered. It is difficult and costly to attempt separation of these closely related isomers.

N. Kobayashi et al., in *Inorg. Chem.*, (1994), 33, 1735–1740, describes the use of large substituents chosen for potential steric inhibition. Kobayashi is directed to reagents for photodynamic therapy. Such reagents must be highly soluble materials which will be transported and selectively attracted to tumor tissue and thereafter can be irradiated to cause an attack on the tumor tissue. The bulky groups in Kobayashi stress the once-planar structure of these molecules out of planarity and prevent the formation of compact, dense, crystal-packing structures.

As a result of the problems associated with the prior art there exists a need for new Pc compounds having improved stability and useful for applications as solar organic photovoltaic materials and as electrophotographic organic photoconductor materials. There is also a need for a method of forming Pc compounds to produce a high yield of a single, favored isomer, ultimately one favoring a selected compact polymorph.

SUMMARY OF THE INVENTION

It has now been found that the addition of bulky substituents on the Pc rings inhibits the production of a compact, desired polymorph. The presence of bulky substituents also reduce the production of the favored polymorph by breaking up the plane-to-plane Van der Waals attraction between planar-packed Pcs.

In addition, it has now been found that in order to avoid disordering the symmetry of the Pc molecule, each arm could be substituted with two identical non-bulky atoms or groups at the paired positions on two sides of the axes (positions 1 and 4; 8 and 11; 15 and 18; and 22 and 25). It has also been found that high reaction yields of uniform, desired polymorphs are obtained when relatively small groups are added as substituents at the inner positions on the Pc rings.

It is an object of the present invention to provide novel Pc compounds for use as dyes for applications as solar organic photovoltaic cells and as electrophotographic organic photoconductor materials.

It is a further object of the invention to provide new methods of forming Pc compounds that reduce the presence of impurities and avoid the formation of mixtures of isomers that are difficult to separate, purify or identify. It is a further object of the invention to provide a novel method of synthesis of pure Pc's, some of which have been substituted to retain two-fold symmetry, $D_{2h}$ or $C_{2v}$, and may be able to deposit in evaporated films or layers with a high yield of a single, desired polymorph.

It is a further object of the invention to produce a selection of inner ring-substituted Pc compounds with an array of desirable electronic levels of selected p-n pairs of dyes to optimize open circuit voltage in the formation of electronic photoconductive or photovoltaic circuits with either perylene compounds or with second Pc's as the active pairs in p-n cells.

Other objects of the invention will be apparent to those skilled in the art to which this invention pertains.

The invention includes phthalocyanine compounds having a structure according to formula I as shown below:

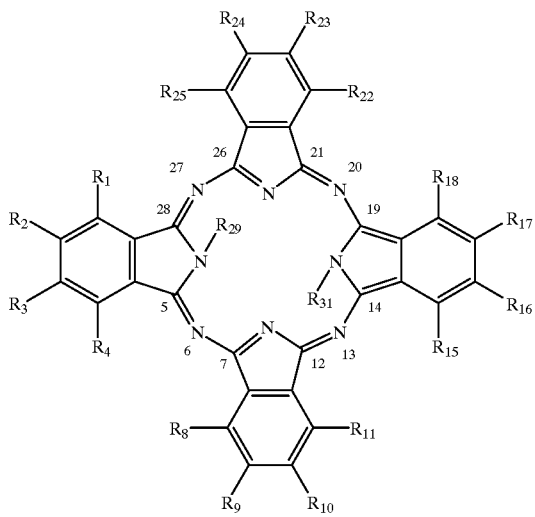

wherein $R_2$, $R_3$, $R_9$, $R_{10}$, $R_{16}$, $R_{17}$, $R_{23}$ and $R_{24}$ are hydrogen, and wherein $R_1$, $R_4$, $R_8$, $R_{11}$, $R_{15}$, $R_{18}$, $R_{22}$, and $R_{25}$ are selected from the group consisting of hydrogen, fluorine, chlorine, methoxy, methyl, ethyl and cyano;

wherein $R_{31}$ and $R_{29}$ are both hydrogen or together are a metal ion having a double positive charge or a metal ion plus non-metal atom or group bound to the metal ion, and having overall a double positive charge; and wherein $R_1$, $R_4$, $R_{15}$, and $R_{18}$ are the same and are a first substituent, and $R_8$, $R_{11}$, $R_{22}$ and $R_{25}$ are the same and are a second substituent which is different from said first substituent.

The invention also includes the synthesis of the novel Pc compounds of the invention. The method includes in part the reaction of an acidic or "A" isoindolinene compound, which is an oxidizing, water sensitive compound, with a basic or "B" isoindolinene compound, which is an electron donor. In a preferred mode of the method of the invention, the A and B compounds react to form a Pc compound that alternates between A and B, e.g., ABAB. The cyclic alteration can be depicted by the notation ABAB, or BABA. Given the two-fold symmetry, these two notations describe the same chemical structure.

DETAILED DESCRIPTION OF THE INVENTION

By "isomer" is meant a substance having a given atomic mass and formula, but differing in atomic arrangement or atomic structure from one or more additional isomers also having this mass and formula.

By "polymorph" is meant a crystalline structure of a particular chemical compound which is structurally different from another possible crystal structure of the same compound.

By "inner position" of a substituent of a Pc compound is meant one located at positions on the benzo rings which are closest to the core of the Pc compound, specifically positions 1, 4, 8, 11, 15, 18, 22 and 25.

By "outer position" of a substituent of a Pc compound is meant one located at positions on the benzo rings which are farthest from the core of the Pc compound, specifically positions 2, 3, 9, 10, 16, 17, 23 and 24.

By "bulky substituent" of a Pc compound is meant a substituent located at any of the inner positions which because of steric hindrance interferes with the ability of the Pc compound to form a stable crystal structure in which the contacts of the overlapping arms of adjacent Pc molecules are minimally disturbed, for example where the plane-to-plane distance is about 3.4 Å or less.

Figure 1:
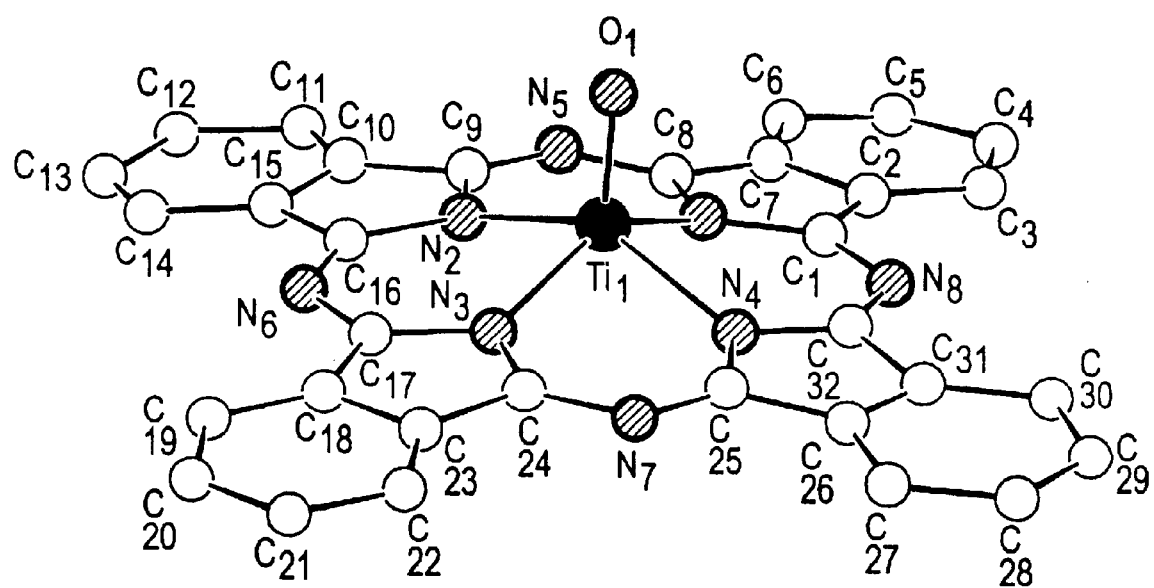
FIG. 1 is a drawing of the molecular structure of a metallized Pc.

Turning now to a detailed description of the drawings, FIG. 1 depicts the molecular structure of a metallized Pc, having a projecting pinning group, in this case TiOPc. The outer part of the molecule is planar, but the titanium atom rises about 0.72 Å and the oxygen atom rises to a total height of about 2.36 Å above the plane. The oxygen has a repulsive radius of about 1.35 Å, so this "pin" rises to a total height of 3.7 Å and prevents the planar portions of molecules in the next layer from packing over the pin. FIG. 1 is a reproduction from a precise crystal structure determination of TiOPc-II by Hiller, et al., Zeit. Kryst., vol. 159, pp. 173–83 (1982). The structure matches a molecular structure of Hiller, et al. obtained from another polymorph, TiOPc-I. TiOPc is a very rigid molecule and there is a very strong van der Waals force acting to pack the flat portions of the molecule at a distance of about 3.4 Å.

Figure 2:
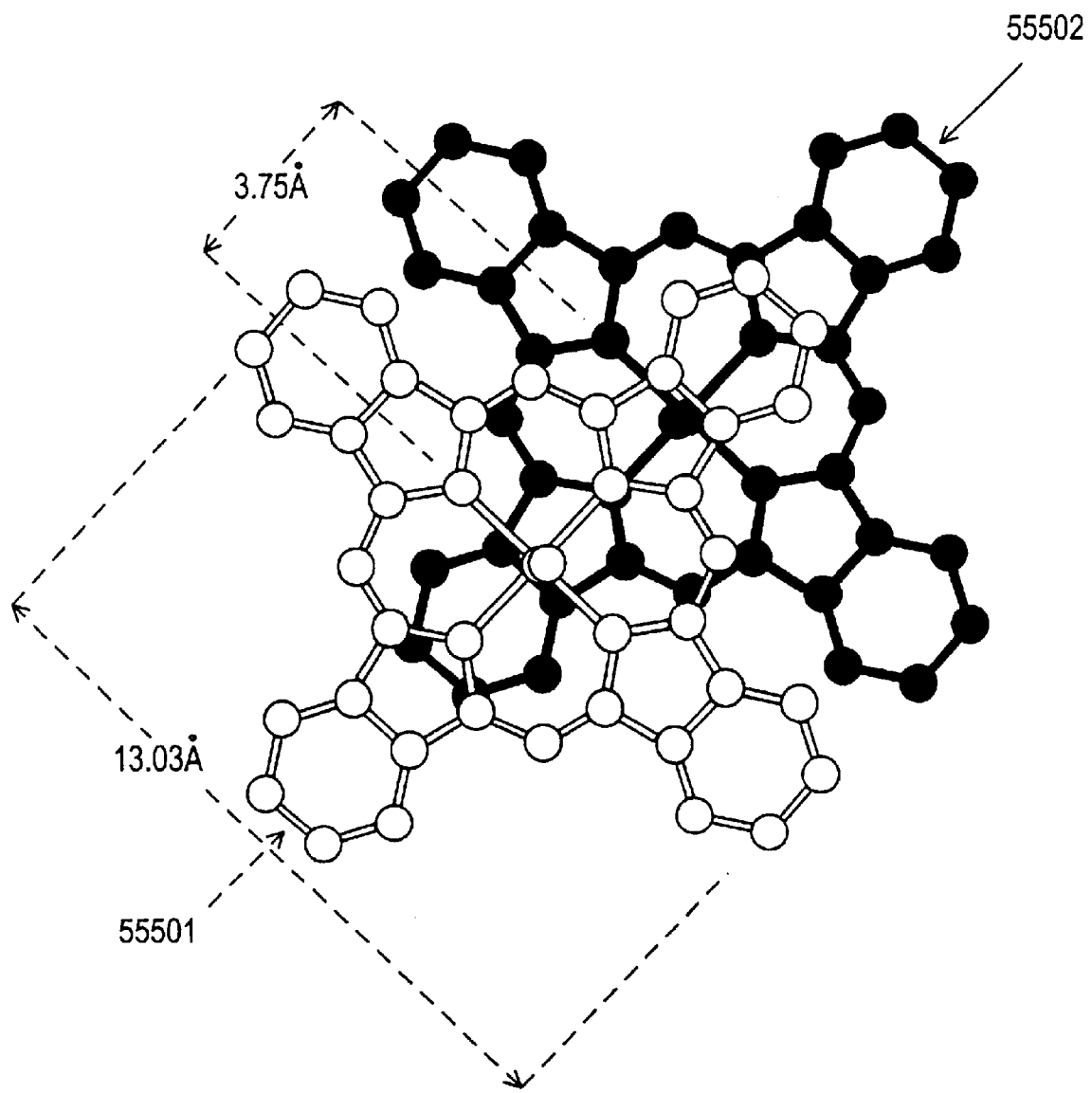
FIG. 2 is a drawing of the crystal structure element of a pair of neighboring Pc dye molecules in TiOPc-II.

FIG. 2 depicts the crystal structure element of the pair of nearest neighbor Pc dye molecules in TiOPc-II. However, this favored structure may also be found in Y—TiOPc.H$_2$O, in HOGaPc-V, and ClAlPc.2H$_2$O. It occurs in every nearest neighbor contact in X—H$_2$Pc, in which the Pc molecules have no pinning group and are completely planar. Thus every molecule in the X— structure has a 3.4 Å facial contact on both sides. As a result, the metal-free Pc molecules can pack together in a manner similar to a stack of poker chips, provided we imagine that the stack has slipped sideways. The presence of this nearest-neighbor structure appears to be necessary but not sufficient to produce a very high efficiency organic photoconductor. FIG. 2 indicates the presence of numerous close contacts in TiOPc-II. However, TiOPc-II is known as only a mediocre photoconductor.

Figure 3A:
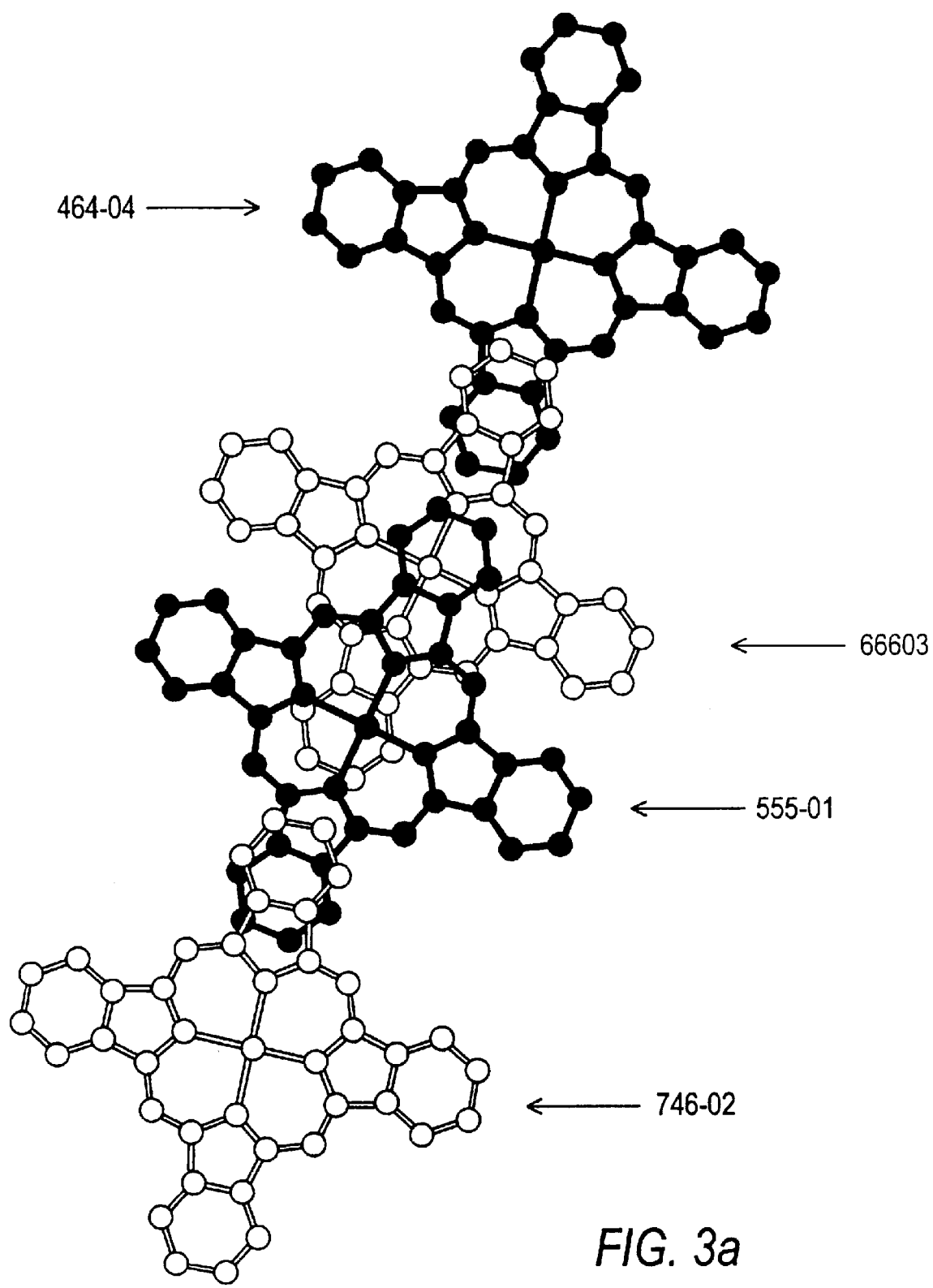
FIGS. 3a and 3b are drawings of Pc molecules in a Y—TiOPc.H$_2$O structure.
Figure 3B:
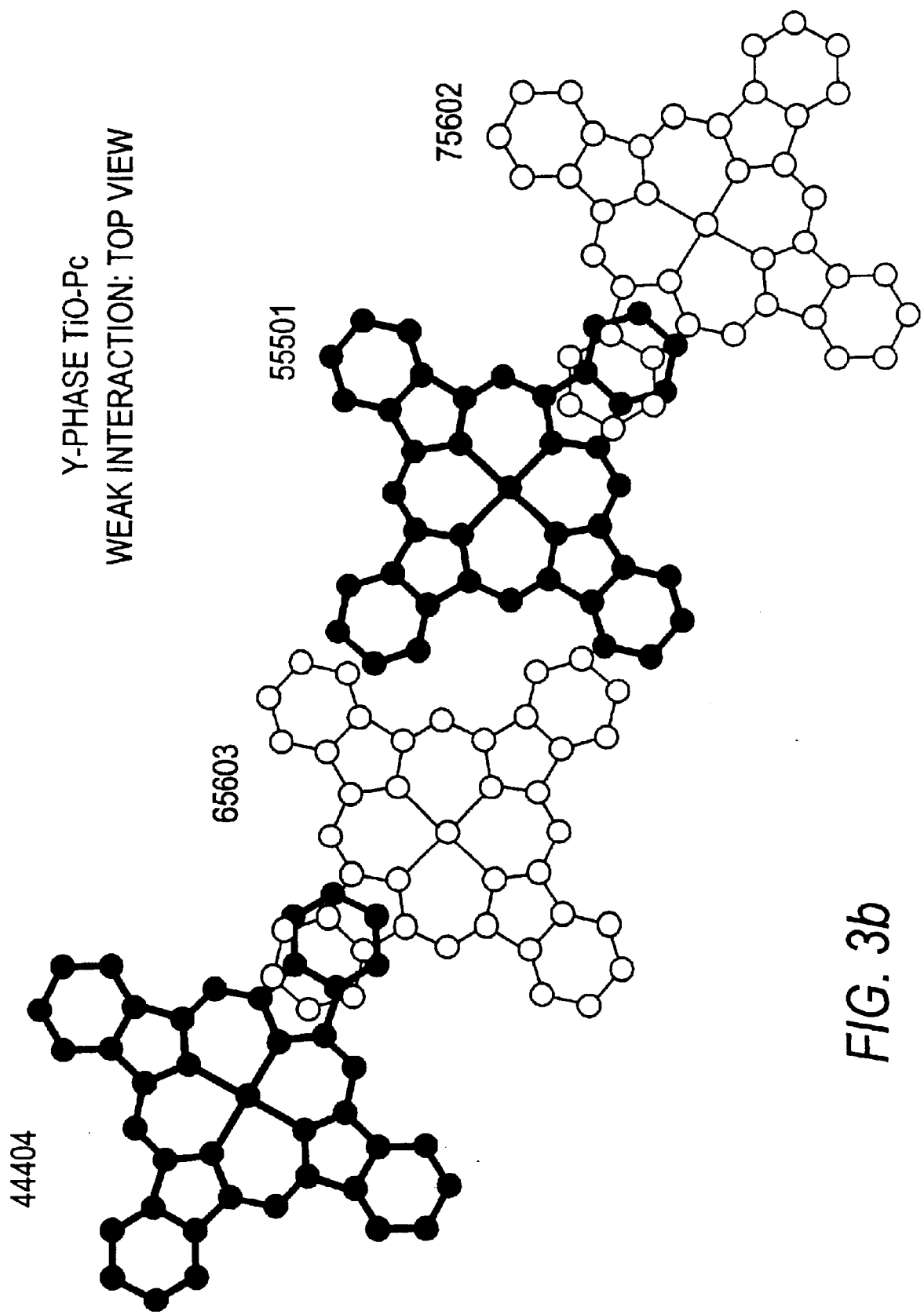

FIG. 2 depicts a monoclinic crystal structure with just two molecules lying in parallel planes in the unit cell. The pair of molecules is identified by the indices 55501 and 55502. The 555 digits identify and locate (x,y,z) the particular unit cell and the 01,02 identify molecules with the pinning group up and down respectively, so that these two molecules can pack unopposed at 3.4 Å. FIGS. 3a and 3b show two sets of four Pc molecules in a Y—TiOPc.H$_2$O structure. Both FIGS. 3a and 3b contain one member of the preferred close-packed pair 55501, and FIG. 3a also shows the other member, 66603. Excitons propagate most rapidly between molecules which are packed face-to-face and it is important that the line and direction set up by the parallel axes of the strongly coupled pairs make a favored axis of polarization for absorption of deep red or NIR light, and also define a favored direction for exciton migration. The next nearest neighbors, 75602 and 46404 cannot pack as closely, but they do overlap somewhat more than a benzene ring. This gently downslanting line depicted in FIG. 3a is coupled medium-strong-medium-strong for exciton transport. In contrast, in FIG. 3b the outer members are coupled about as well as the outer members in FIG. 3a, but the central contact, 55501 over 65603, is broken- not quite to a limit of zero coupling for propagation, but much weaker. As a result, the coupling for exciton transport along this line is medium-weak-medium-weak.

Extensive overlap and plane-to-plane contacts in FIG. 3a favor rapid exciton transport in this column direction throughout a crystal domain or even across a narrow gap between domains. The structure shown in FIG. 3b contains one molecule of the stack shown in 3a. The contacts for exciton transfer are strong-medium-strong-medium in FIG. 3a, but medium-weak-medium-weak in FIG. 3b.

The packing structure of TiOPc-II is depicted in FIG. 4, again emphasizing the preferred contact, now 55501 over 55502. However, the direction of strong coupling is cocked at almost 45° to the logical sense of propagation, as defined by molecular centers. Exciton propagation is present, since the process of charge separation after absorption of a photon has to be promoted by bringing the excitons to some local point or zone where there is an electrical field strong enough to promote the separation. Exciton propagation in p-n organic solar cells is desirable to bring excitons to a field existing at the p-n interface as a result of designing electron donor and acceptor dyes to give or receive electrons to create a field at their interface. In electrophotography, one tries to bring the excitons to the surfaces of the microcrystal absorber/sensitizers where they can encounter aromatic polyamine electron donors dissolved at high concentration in the polymeric support medium. The polyamines are selected for electrochemical potentials which favor electron transfer into the exciton-bearing crystal.

Figure 4:
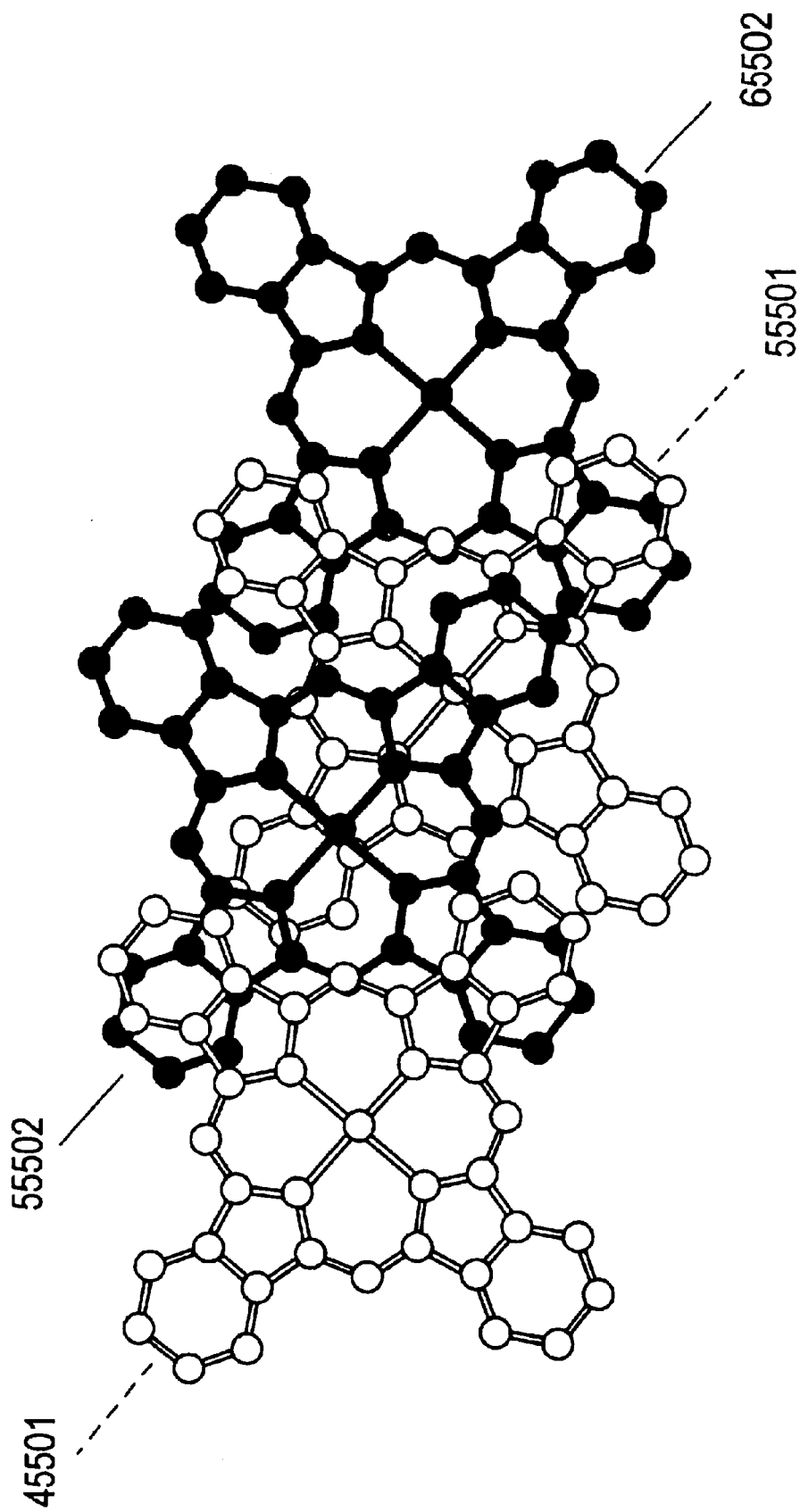
FIG. 4 is a drawing of four Pc molecules in the crystal structure of TiOPc-II.

FIG. 4 is a companion drawing of four Pc molecules in the crystal structure of TiOPc-II showing weak-strong-weak-strong coupling elements, but with angular contacts to give strong-weak-strong-weak contact between molecules at about the worst possible angle for exciton propagation, approximately 45°.

The invention comprises novel Pc compounds of formula I, wherein the substituents $R_1$, $R_4$, $R_8$, $R_{11}$, $R_{15}$, $R_{18}$, $R_{22}$ and $R_{25}$ are selected from the group consisting of hydrogen, fluorine, chlorine, methyl, ethyl, methoxy and cyano. The invention comprises in part the selection of small, non-bulky substituents at the inner positions. The substituents are selected so that there is little interference between the substitutents located at the inner positions of the various benzo rings of the Pc compound, and the planarity of the Pc rings contains approximately a "graphitic distance" or an average plane-to-plane distance of no more than 3.4 Å.

In one embodiment, the substituents at inner positions 1, 4, 15, 18, are the same and are a first substituent, and the substitutents at inner positions 8, 11, 22 and 25 are the same and are a second substituent, which is different from the first substituent. The invention consists in part in the production of Pc compounds with substituent groups capable of fitting in pairwise opposition at the 1, 4, 8, 11, 15, 18, 22, and 25 positions. In this embodiment the substitutents are selected so that there is little steric hindrance caused by the substitution at the area between positions 1 and 25; 4 and 8; 11 and 15; and 18 and 22.

Thus, in one embodiment the invention comprises tetra-substituting at the 1, 4, 15 and 18 positions with a single selected group and with a second selected group at 8, 11, 22 and 25. For structural adjustment to favor X— or Y— polymorphs it may be desirable to use a relatively bulky substituent (—O—CH$_3$) at the first set of positions but a smaller substituent such as —F at the facing 8, 11, 22, and 25 positions. The internal attractions may also make this tetra-OCH3, tetra-F Pc compound a highly stable material with these four extra internal contacts. It would be expected to be a molecule with exemplary chemical and photochemical stability, even among Pc's.

Table I below provides a list of some of the relatively small substituents contemplated by the invention. In general, the substituents may be used singly with —H as the second inner substituent or in pairs. The invention contemplates pairing of the largest groups such as —CH$_2$CH$_3$ or C≡N, with the smaller groups such as H, F and CH$_3$.

TABLE 1

Substituents Contemplated by the Invention

| Substituent | Chemistry |
| --- | --- |
| Hydrogen atom | stable, normal periphery substituent |
| Fluorine atom | stable substituent which greatly enhances electron acceptance |
| Methoxy group | stable, fits loosely, greatly enhances. electron donation |
| Methyl group | does not fit with another methyl group, may interact positively with —Cl or —F; slight enhancement of electron donation |
| Chlorine atom | Fairly stable, very tight fit with another Cl atom, may fit tightly and give higher stability with —CH$_3$ |
| Cyano- (CN) | Very stable, but may enter into competitive coupling reactions to disrupt phthalocyanine synthesis |
| Ethyl | A larger group than the others but can be fitted against smaller contacting groups. |

Figure 5:
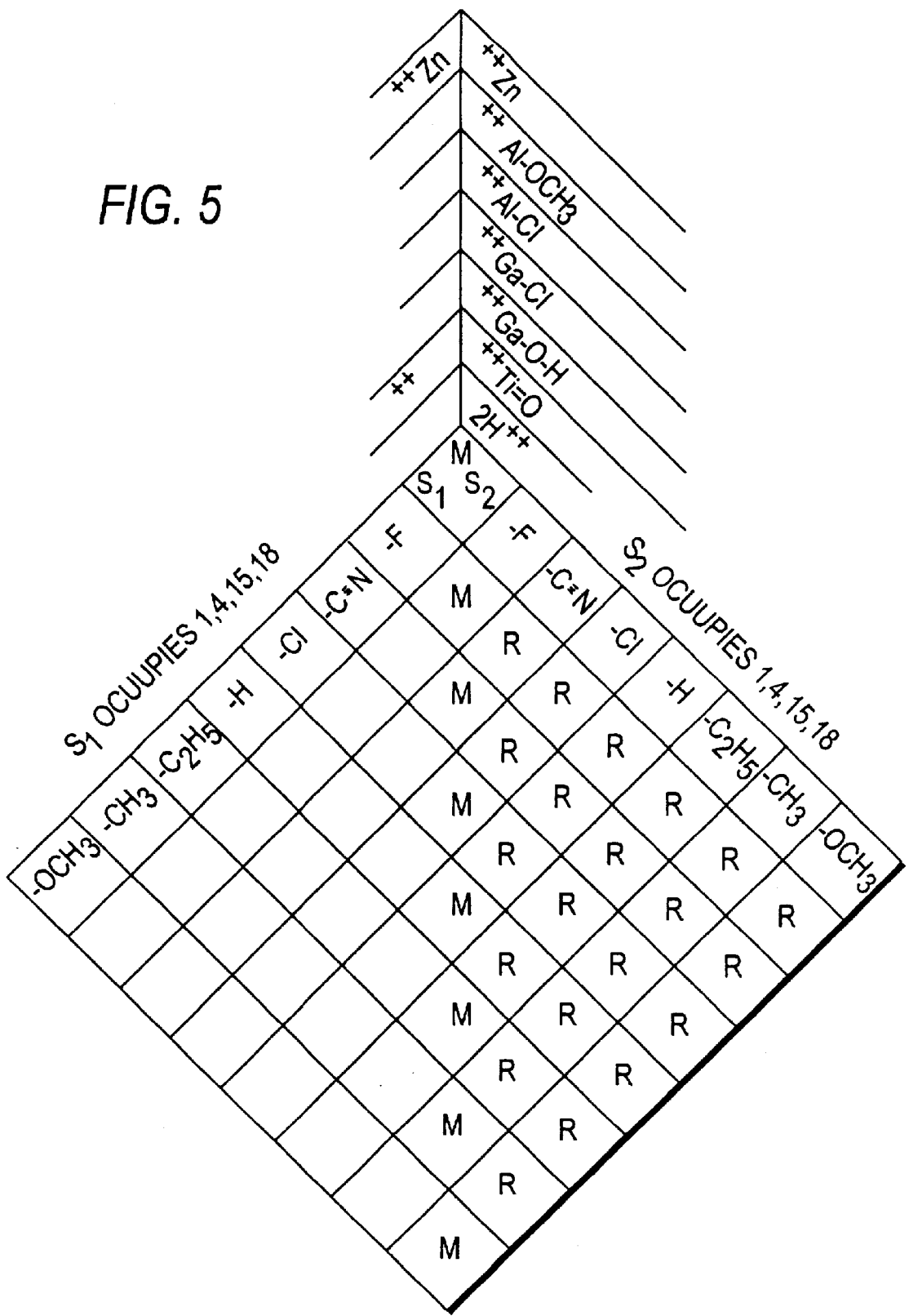
FIG. 5 is a table showing the possible Pc compounds of the invention.

FIG. 5 shows the compounds of the invention, wherein $S_1$ are the substituents for inner positions 1, 4, 15 and 18, and $S_2$ are the substituents for inner positions 8, 11, 22 and 25. Compounds represented by M are phthalocyanines with substitution at all inner positions by single substituent. Monosubstituted Pc compounds of the invention with —CH$_3$, C$_2$H$_5$, and C≡N are a crowded fit according to Corey-Pauling-Koltun or "CPK" modeling, and consequently may have lower synthetic yields that the other monosubstituted Pc's of the invention. The existence of any of these or of the corresponding sixteen-group substituted Pc compounds gives some indication that the group can fit against itself. The compounds represented by R are contemplated by the invention. Note that the surface of available reactant combinations of FIG. 5 is half empty because rotating the Pc by 90° around the actual or figurative M—X or M=O axis exchanges the $S_1$ and $S_2$ columns without creating a new molecule.

The method of the invention calls for the formation of an inner-substituted metal-free H$_2$Pc, optionally followed by a metallization reaction which displaces 2H$^+$ with a metal, or metal-containing group. The method of the invention is based on the Scheme VII method described by Leznoff and Lever in the aforementioned "Phthalocyanines, Properties and Applications," which has been incorporated by reference. The Scheme VII method of Leznoff and Lever at page 14 is enhanced in part by the production of new substituted Pc's via synthetic reactions which produce single isomer products. The first step of the reaction forms a H$_2$Pc compound, after which the H$_2$Pc compound may optionally be reacted with a metallizing reagent to form a metallized Pc or metallophthalocyanine, having a core metal ion or metal-containing group.

Table II below presents a list of favored metals for use according to the invention in metallized PCs:

TABLE II

| Metal | Atomic Number | Rank of Abundance in Earth Crust | Most Likely Compound Formed in Pc Core |
| --- | --- | --- | --- |
| Titanium (Ti) | 22 | 9 | TiOPc H$_2$O |
| Gallium (Ga) | 31 | 37 | HOGaPc; ClGaPc;H$_3$COGaPc |
| Aluminum (Al) | 13 | 3 | ClAlPc; H$_3$COAlPc |
| Scandium (Sc) | 21 | 46 (not conc.) | ClScPc; H$_3$COScPc |
| Zinc | 30 | 23 | ZnPc |
| H$_2$$^{++}$ | 1 | 11 | H$_2$Pc |

As is understood by those of ordinary skill in the art, the synthesis of samples of desirable crystal structures of Pc's requires heat or shared chemical energy in the form of highly reactive starting materials. Pc's which have a favorable crystalline structure, such as those which fit together as Corey-Pauling-Koltun or "C.P.K." models or as complete crystal structures can usually be synthesized at temperatures of 200° to 260° C. For example, as described in R. O. Loutfy, A. M. Hor, G. DiPaola-Baranyi, and C. K. Hsiao, *Journal of Imaging Science* (1985) 29, pp. 116–21, a Pc compound can be formed by the reaction of one mole part AlCl$_3$ to three mole parts phthalonitrile to form ClAlPc with a single chlorine atom projecting outward. An increase in the reaction temperature from the usual 200° to 225° C. results in a rising mixture of substituted Pc product with one or more additional chlorines in the outer positions. Because of the inability of prior art methods of synthesis to produce a single favored isomer, the product will be contaminated by ClAlPcCl, a ring-chlorinated $^{++}$Al—Cl material, almost sure to be chlorinated at one or more of the outer positions (positions 2,3; 9,10;16,17;23,24).

The possible advantages of lower temperature reactions to form Pc's have long been appreciated. An early advance came with the realization that in the direct syntheses with B-only phthalonitriles, the amino-iminoisoindolinenes made by adding one molecule of ammonia per phthalonitrile to make an alternant reactant was, in fact, making a catalyst for the direct phthalonitrile reaction. Prior known methods invove the formation of a modest quantity of amino-iminoisoindolinene and adding it to the nitrile, of making the pure catalyst, or using a phthalonitrile that reacts under anhydrous ammonia to make a running synthesis with catalyst provided in situ. It is also possible to use less reactive metallating reactants such as zinc diacetate Zn(CH$_3$COO)$_2$ to make planar ZnPc's, or Ti(— OCH$_2$CH$_2$CH$_2$CH$_3$)$_4$ for pinned titanyl derivatives. These variations lower the running temperatures to 120–180° C. and also reduce side reactions. Leznoff et al., "The Synthesis of Phthalocyanines at Room Temperature", (1996) *Chem. Comm.*, February 1, pp. 1245–6, uses the very strong base lithium-2,2-dimethylaminoethoxide, and drops the required reaction temperature to room temperature (24° C.) or below.

Grammatica et al., "Improved Synthesis of Metal-free Phthalocyanines, ", *J. Hetero. Chem.* (1970) 7, 1403–1405 (1970) describes an early improvement in the synthesis of metal-free Pc's by promoting the dialkylaminoethanol from catalyst to solvent, and so reducing those reaction temperatures to reflux temperatures such as 133° C. in dimethylaminoethanol, obtaining yields of 90–50% in the process. Other alkyl- groups such as ethyl-, propyl-, or butyl- have been added to the ethanolamine to select higher reflux temperatures.

Austrian Patent 267,711 (Wimmer) (1969), describes a class of substituent-directing reactions, but does not describe how rapid energy-rich reaction mixtures could react, even below room temperature. Leznoff, et al., *Phthalocyanines, Properties and Applications* has shown that Wimmer's reaction temperatures as high as 140° C. brought in the classical B-only phthalocyanine reaction and other contaminants, such as BBAB U.S. Pat. No. 4,061,654 to Idelson, does not describe an analysis of reaction rates, and was silent as to the actual temperature(s) for the exemplary of reactions. It is possible that some of the reagents or solvents described in Idelson were contaminated with water, so that the reactions ran on whatever was left of the trihalo-isoindolinene. The yields described in Idelson were considerably below more recent reactions.

Young and Onyebuagu, "Synthesis and Characterization of Di-disubstituted Phthalocyanines," J. Org. Chem. 1990, 55, pp. 2155–59, hereby incoporated by reference, describe well controlled reactions. Young describes a process involving the exclusion of water and the initiation of reactions at 0° C., holding the temperature steady for one hour, and then letting the reaction mix warm to room temperature. The resulting reaction after six hours combined isomeric purity with a relatively high reaction yield.

In addition, Young et al. describe a reaction that accounts for the fundamentally "wet" quality of the reduction step. The reaction involves filtering out the precipitated triethylamine-hydrochloride at the end of the A+B macrocycle-forming reaction to remove a potentially troublesome HCl-scavenging system. Only then could the reduction reaction involving hydroquinone and sodium methoxide be run without interference, and the reaction be considered complete. The product was washed repeatedly with boiling water, then with with boiling ethanol until no color could be seen in either Pc non-solvent.

Young et al. describe yields of up to 48%, 48%, and 17%. The isomerization is not controlled, except for placing one substituent on opposite arms, e.g., any of 1,2,3,4 and 15,16, 17, or 18, for example. However, the substituents are bulky. The two largest yields described in Young et al. were obtained with bis-(4-t-butylphenoxy-) groups on two opposite arms in the first case and bis-(4-cumylphenoxy-) in the second case. Young et al. also describe symmetry breaking of the original D$_{4h}$ phthalocyanine chromophore by two phenoxy groups on opposite arms to give a splitting of the single, degenerate absorption band into two bands of crossed symmetry which show a splitting of only 13–18 nm, as compared to the 45 nm splitting made by the simple 2H+ substitution on ordinary H$_2$Pc. As long as this splitting is smaller than the transition density broadening of the longest wavelength (red) absorption band, a broad and nearly featureless absorption system from about 500 nm to about 820 nm will result.

In order to exemplify the results achieved using the method of the invention the following examples are provided without any intent to limit the scope of the instant invention to the discussion therein.

The method of the invention first involves the formation of the A and B isoindolinene compounds which are later reacted to form the $H_2Pc$ compound.

The o-phthalic anhydrides substituted 3,6-difluoro- and 3,6-dichloro- are commercially available. The synthesis of 3,6-dimethyl and 3,6-dimethoxyphthalimides or phthalonitrites is within the practice of those of ordinary skill in the art. The method of the invention consists in part of the formation of Pc's by the use of exclusively doubly inner-substituted phthalonitriles or indolinenes, such as 3,6-dimethyl phthalonitrile or 3,6-difluorophthalonitrile, as the "B" compound.

The first step of the reaction involves an acidic isoindolinene compound or "A", such as 1,3,3'-trichloro isoindolinene, which is an oxidizing, acidic water-sensitive compound which can release HCl. The chemical structure of 1,3,3'-trichloro isoindolinene is depicted below:

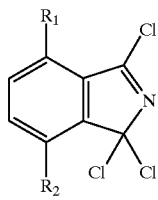

$R_1$ and $R_2$ may be any of the substituents listed in Table 1. Preferred acidic isoindolinene compounds are substituted with a group selected from F, C≡N, Cl or H.

Also required is a basic isoindolinene compound or "B" which is an electron donor, is not water sensitive, and under classic phthalocyanine synthesis conditions can incorporate 2N atoms from each isoindolinene to form BBBB Pc compounds. A typical "B" compound is 4,7-dimethyl-1,3,3'-aminoindolinene, which is depicted below:

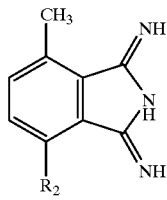

Substituted phthalic acid derivatives and the requisite phthalimides are commercially available. Each synthesis requires the isoindolinene derivative of one corner arm and the trichloroisoindolinene of the other arm. Unsubstituted isoindolinenes, in which both the $R_1$ and $R_2$ group are H, are commercially available. Phthalimide is also commercially available. Additional substituted isoindolinenes and trichloroisoindolinenes are within the knowledge and skill of those of ordinary skill in the art. Preferred basic isoindolinene compounds are substituted with a group selected from $OCH_3$, $CH_3$, and $C_2H_5$.

Another example of the method of the invention is the substitution of methyl fragments via 4,7-dimethylaminoimino-phthalimide. The formation of the materials to make this isoindolinene are within the knowledge of a person of ordinary skill in the art.

The initial steps for the method of the invention is the production of the A and B compounds. These compounds must be prepared separately and stored in the anhydrous state.

As set forth below, the first reaction to make the 4,7 dimethyl compound is the reaction of 2,4-hexadiene and maleimide according to the steps described to form the isoindolinene "B" compound.

First, the reactants undergo a Diels-Alder reaction, in which the carbon-carbon double bonds break and a ring structure is formed. Thereafter, the reactants undergo a catalytic dehydrogenation. Afterwards, the reactants are contacted with $NH_3$ and then contacted with acetic anhydride resulting in dehydration. Finally, the reactants are again contacted with $NH_3$.

The overall reaction to form this particular compound, 4,7-dimethyl-1,3,3'-indoimino phthaloindolinene is depicted below:

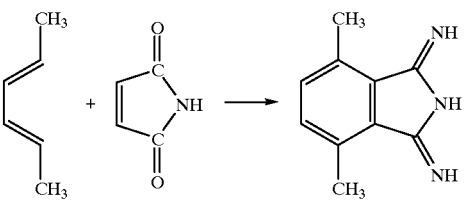

The second step is the formation of the similar isoindolinene "A" compound, as shown below wherein $R_1$ is Cl or F.

Finally, the A and B compounds are combined to form desired Pc compounds of the invention.

The reaction of the invention has been reported to occur significantly at 0° C. temperature within one hour, and to go to completion in some six hours, with groups having very bulky substituents. A typical reaction mixture brings the two A,B components together in dehydrated tetrahydrofuran together with a modest excess of triethylamine, which acts as a weak base and scavenges the reactive HCl which is liberated. The reactants and solvent must be kept absolutely water free to prevent loss of the trihaloisoindolinene. For small scale reactions this is best done in a dehydrated glove box regime. The Pc ring is apparently formed at low temperatures in this mixture. Once formation is complete or maximized, the reaction mix is filtered to remove triethylamine, and the precursor compound is reduced by $2e^-$ by hyrdoquinone to form the stable $H_2Pc$. The reaction is thereafter run as a "wet" reaction with hydroquinone and sodium methoxide in methanol. The water sensitivity ceases with the reduction reaction, and the product phthalocyanine may or may not take up water of crystallization, which can be driven off by mild heating and vacuum treatment, if necessary. Water sensitivity of the A component is easier to handle on a pilot or full production scale system, simply because the surface-to-volume ratio drops markedly, and blanketing with inert gases is a routine process procedure.

It is noted that the A species contains only a single nitrogen atom, and thus is unable to form a Pc compound of the type "AAAA", since it must join with another intermediate to obtain a total of 8 nitrogen atoms. Species B, the 1, 3, 3' aminoindolinene, is a reducing agent and base which can be formed by treating the chosen phthalonitrile with anhydrous ammonia. The B species can form a conventional Pc of four B units, "BBBB", or in the absence of sufficient concentrations of A it can form a compound impurity Pc such as BBAB. The side reaction to form the impurity can be minimized by maintenance of low temperatures and the absence of catalysts.

The Pc may then be reacted with a metallizing reagent, such as for example $TiCl_4$, $TiO(AcAc)_2$, $AlCl_3$, $GaCl_3$, $Ga(AcAc)_3$, $Zn(Ac)_2$, etc., to form a metal Pc.

In order to further ensure the production of the desirable ABAB Pc sequence over the undesirable BBBA or BBBB it is important to not heat the reaction beyond the lowest practical reaction temperature, avoid the presence of catalysts that will lead to the formation of a BB product, and maintain the relative concentrations of the A and B species so that the concentration of A is somewhat greater than the concentration of B. It is expected that the reaction will favor formation of ABAB if a continuous feed reactor is used.

The invention is also directed to a selection of inner ring-substituted Pc compounds with an array of desirable electronic levels of selected p-n pairs of dyes to optimize open circuit voltage in the formation of electronic photovoltaic cells, photoconductive or photovoltaic circuits with either perylene compounds or with second Pc's as the active pairs in p-n cells. Photovoltaic cells with perylene compounds are described by J. P. Whitlock, et al, in "Investigations of Materials and Device Structures for Organic Semiconductor Solar Cells," *Optical Engineering*, vol. 32, pp. 1921–34 (1993), which is hereby incorporated by reference; and G. Bird, "A Critical Test of Organic P—N Photovoltaic Cells", Conference Booklet, National Renewable Energy Laboratory of the U.S. Department of Energy, Feb. 5, 1996, Estes Park, Colo., which is hereby incorporated by reference.

An exemplary photovoltaic cell contemplated by the invention may comprise a first layer comprising indium tin oxide; a second layer comprising a compound selected from the group consisting of a perylene derivative, or any of various metallophthalocyanine compounds herein described, such as $ZnC_{32}F_{16}N_8$, or metallophthalocyanine compounds which include a core atom selected from the group consisting of $M^{++}$, $M^{++}=O$ or $M^{++}$—Cl. The second layer is disposed in contact with a third layer, which comprises a Pc of the invention. A fourth layer, which is a metallic conductive layer, such as silver, is disposed in contact with the third layer and forms a matched contact with a minimal resistance with the third layer.

The scope of the following claims is intended to encompass all obvious changes in the details, materials, and arrangement of parts that will occur to one of ordinary skill in the art.

What is claimed is:

1. A photovoltaic cell comprising a phthalocyanine layer comprising a compound of formula (I):

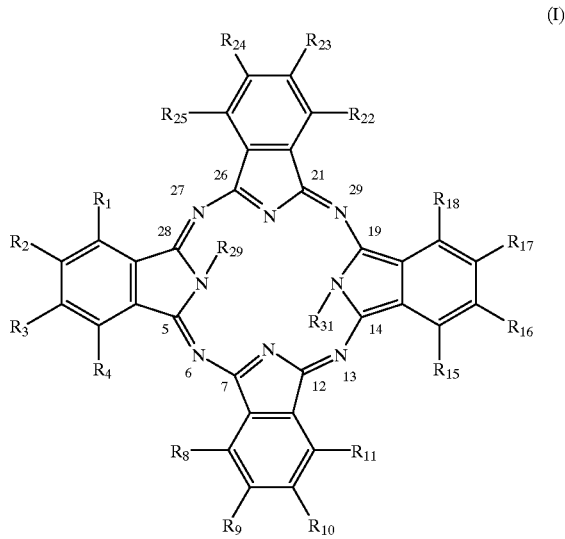

wherein $R_2$, $R_3$, $R_9$, $R_{10}$, $R_{16}$, $R_{17}$, $R_{23}$ and $R_{24}$ are hydrogen;

$R_1$, $R_4$, $R_8$, $R_{11}$, $R_{15}$, $R_{18}$, $R_{22}$ and $R_{25}$ are selected from the group consisting of hydrogen, fluorine, chlorine, methoxy, methyl, ethyl and cyano;

$R_{29}$ and $R_{31}$ are both hydrogen or together are a metal ion having a single valence or a metal ion and non-metal ion or group bound to the metal ion; and $R_1$, $R_4$, $R_{15}$, and $R_{18}$ are the same, and are a first substituent, and $R_8$, $R_{11}$, $R_{22}$, and $R_{25}$ are the same and are a second substituent which is different from said first substituent; and a metallic conductive layer disposed in contact with said phthalocyanine layer to form a matched contact with a minimal resistance.

2. The photovoltaic cell according to claim 1 further comprising a compound layer disposed in contact with said phthalocyanine layer, said compound layer comprising a compound selected from the group consisting of a perylene derivative, $ZnC_{32}F_{16}N_8$, and a metallophthalocyanine comprising a core atom selected from the group consisting of $M^{++}$, $M^{++}=O$ and $M^{++}$—Cl, wherein M represents a metal ion or metal ion plus non-metal atom or group bound to the metal ion.

3. The photovoltaic cell according to claim 2, further comprising a layer comprising indium tin oxide disposed in contact with said compound layer.

4. The photovoltaic cell according to claim 1, wherein $R_1$, $R_4$, $R_{15}$ and $R_{18}$ of formula (I) are fluorine.

5. The photovoltaic cell according to claim 1, wherein $R_1$, $R_4$, $R_{15}$ and $R_{18}$ of formula (I) are cyano.

6. The photovoltaic cell according to claim 1, wherein $R_1$, $R_4$, $R_{15}$ and $R_{18}$ of formula (I) are chlorine.

7. The photovoltaic cell according to claim 1, wherein $R_1$, $R_4$, $R_{15}$ and $R_{18}$ of formula (I) are ethyl.

8. The photovoltaic cell according to claim 1, wherein $R_1$, $R_4$, $R_{15}$ and $R_{18}$ of formula (I) are methyl.

9. The photovoltaic cell according to claim 1, wherein $R_1$, $R_4$, $R_{15}$ and $R_{18}$ of formula (I) are methoxy.

10. The photovoltaic cell according to claim 1, wherein in Formula (I), $R_8$, $R_{11}$, $R_{22}$ and $R_{25}$ are fluorine.

11. The photovoltaic cell according to claim 1, wherein $R_8$, $R_{11}$, $R_{22}$ and $R_{25}$ of formula (I) are cyano.

12. The photovoltaic cell according to claim 1, wherein in Formula (I), $R_8$, $R_{11}$, $R_{22}$ and $R_{25}$ are chlorine.

13. The photovoltaic cell according to claim 1, wherein $R_8$, $R_{11}$, $R_{22}$ and $R_{25}$ of formula (I) are ethyl.

14. The photovoltaic cell according to claim 1, wherein in Formula (I), $R_8$, $R_{11}$, $R_{22}$ and $R_{25}$ are methyl.

15. The photovoltaic cell according to claim 1, wherein $R_8$, $R_{11}$, $R_{22}$ and $R_{25}$ of formula (I) are methoxy.

16. The photovoltaic cell according to claim 1, wherein $R_{29}$ and $R_{31}$ of formula (I) together comprise a metal selected from the group consisting of titanium, gallium, aluminum, scandium and zinc.

17. The photovoltaic cell according to claim 1, wherein the compound of formula (I) is in crystalline form.

18. The photovoltaic cell according to claim 17, wherein said crystalline form consists essentially of a single polymorph.

19. A photovoltaic cell comprising
a first layer comprising indium tin oxide;
a second layer comprising a compound selected from the group consisting of a perylene derivative, $ZnC_{32}F_{16}N_8$, and a metallophthalocyanine comprising a core atom selected from the group consisting of $M^{++}$, $M^{++}=O$ and $M^{++}-Cl$ wherein M represents a metal ion or a metal ion plus non-metal atom or group bound to the metal ion; said second layer disposed in contact with said first layer;
a third layer comprising a compound of formula (I) below in crystalline form, said third layer disposed in contact with said second layer;

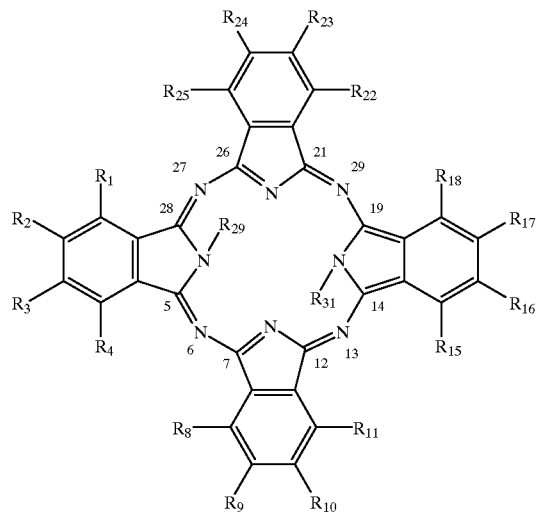

wherein
$R_2$, $R_3$, $R_9$, $R_{10}$, $R_{16}$, $R_{17}$, $R_{23}$ and $R_{24}$ are hydrogen;
$R_1$, $R_4$, $R_8$, $R_{11}$, $R_{15}$, $R_{18}$, $R_{22}$ and $R_{25}$ are selected from the group consisting of hydrogen, fluorine, chlorine, methoxy, methyl, ethyl and cyano;
$R_{29}$ and $R_{31}$ are both hydrogen or together are a metal ion having a single valence or a metal ion and non-metal ion or group bound to the metal ion; and
$R_1$, $R_4$, $R_{15}$, and $R_{18}$ are the same, and are a first substituent, and $R_8$, $R_{11}$, $R_{22}$, and $R_{25}$ are the same and are a second substituent which is different from said first substituent; and
a fourth metallic conductive layer, said fourth layer disposed in contact with said third layer, wherein said third and fourth layers form a matched contact with a minimal resistance.

* * * * *